US012691252B2

(12) United States Patent
Kameoka et al.

(10) Patent No.: US 12,691,252 B2
(45) Date of Patent: Jul. 28, 2026

(54) METHOD FOR MANUFACTURING CATHETER, AND CATHETER

(71) Applicant: NIPRO CORPORATION, Osaka (JP)

(72) Inventors: Koji Kameoka, Osaka (JP); Yoshihiro Mori, Osaka (JP); Emi Kusakabe, Osaka (JP)

(73) Assignee: NIPRO CORPORATION, Osaka (JP)

( * ) Notice: Subject to any disclaimer, the term of this patent is extended or adjusted under 35 U.S.C. 154(b) by 506 days.

(21) Appl. No.: 18/256,993

(22) PCT Filed: Dec. 7, 2021

(86) PCT No.: PCT/JP2021/044950
§ 371 (c)(1),
(2) Date: Jun. 12, 2023

(87) PCT Pub. No.: WO2022/145179
PCT Pub. Date: Jul. 7, 2022

(65) Prior Publication Data
US 2024/0058572 A1 Feb. 22, 2024

(30) Foreign Application Priority Data

Dec. 28, 2020 (JP) ................................. 2020-218281

(51) Int. Cl.
*A61M 25/00* (2006.01)
(52) U.S. Cl.
CPC ...... *A61M 25/005* (2013.01); *A61M 25/0012* (2013.01); *A61M 25/0045* (2013.01)
(58) Field of Classification Search
CPC ............ A61M 25/005; A61M 25/0012; A61M 25/0045
See application file for complete search history.

(56) References Cited

U.S. PATENT DOCUMENTS 6,562,022 B2 * 5/2003 Hoste .................. A61M 25/005
604/524
9,486,605 B2 * 11/2016 Ravichandran ...... B23K 1/0008
(Continued)

FOREIGN PATENT DOCUMENTS

CN 103566449 A 2/2014
JP 2001161824 A 6/2001
(Continued)

OTHER PUBLICATIONS

International Search Report from International Application No. PCT/JP2021/044950 mailed Jan. 25, 2022.
(Continued)

*Primary Examiner* — Dung T Ulsh
(74) *Attorney, Agent, or Firm* — Ballard Spahr LLP

(57) ABSTRACT

This method for manufacturing a catheter involves manufacturing a catheter that includes a braided body having a first element wire and a second element wire intersecting the first element wire, and an outer layer provided on the outer circumference of the braided body, the method comprising: a coating step in which the outer-circumferential side of the braided body is coated with a laser-light-transmissive coating member; a cutting step in which a portion of the first element wire and/or the second element wire in the braided body is irradiated with laser light from the outer side of the coating member and the element wire is cut, said portion being positioned further toward the distal-end side than an intersecting part; and a removal step in which the coating member is removed from the outer-circumferential side of the braided body.

5 Claims, 13 Drawing Sheets

(56)                  References Cited

U.S. PATENT DOCUMENTS

| | | |
|---|---|---|
| 2008/0125752 A1 | 5/2008 | Gunderson et al. |
| 2012/0109078 A1 | 5/2012 | Schaeffer |
| 2014/0031796 A1 | 1/2014 | Nishigishi et al. |
| 2014/0046301 A1* | 2/2014 | Kuwada .............. A61M 25/005 |
| | | 604/527 |
| 2014/0214006 A1 | 7/2014 | Hiroshige et al. |
| 2016/0121075 A1 | 5/2016 | Schaeffer |
| 2017/0072166 A1* | 3/2017 | Hiroshige ........... A61M 25/005 |

FOREIGN PATENT DOCUMENTS

| | | | |
|---|---|---|---|
| JP | 2005-230318 | * | 9/2005 |
| JP | 2014023811 A | | 2/2014 |
| JP | 6080258 B2 | | 1/2017 |
| WO | 2011008738 A1 | | 1/2011 |

OTHER PUBLICATIONS

Extended European Search Report for European Application No. 21915040.6 mailed Jun. 25, 2024.

* cited by examiner

F I G . 1
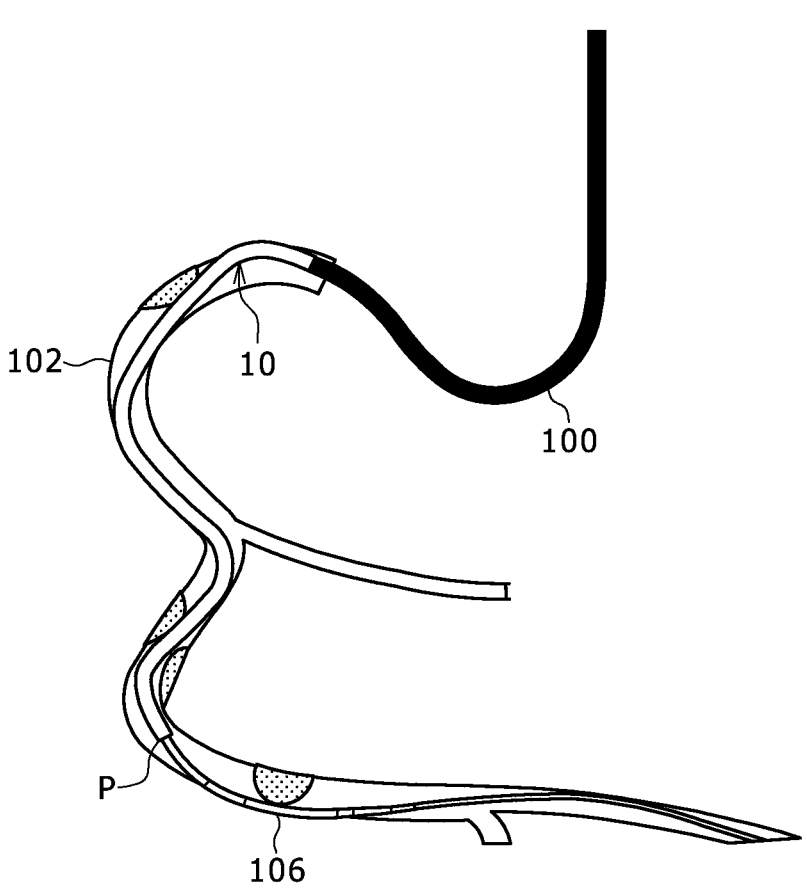

F I G . 3
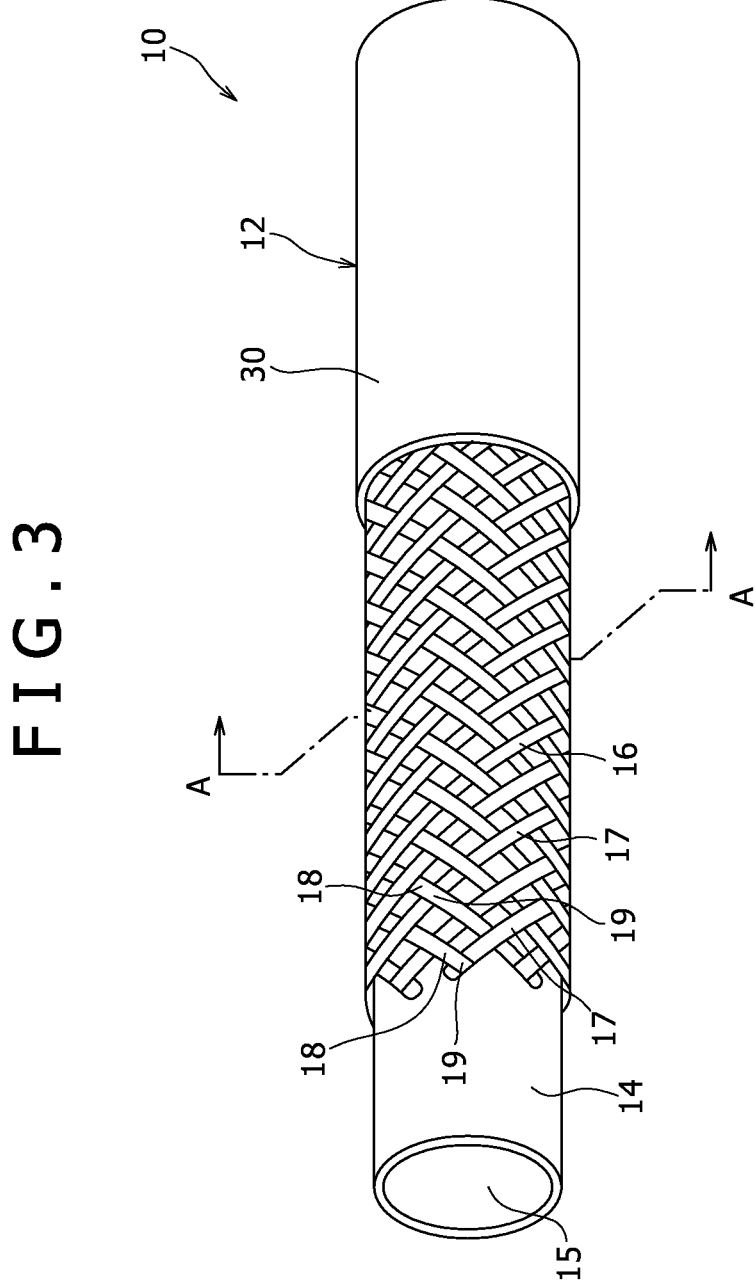

TIP SIDE

F I G . 8
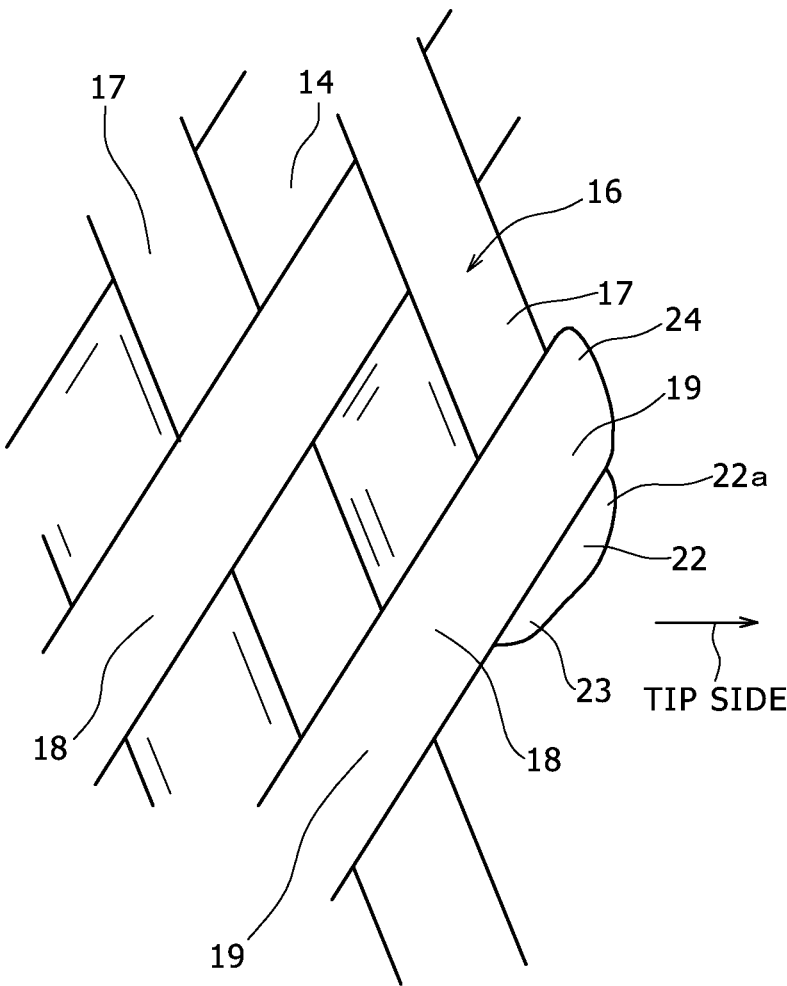

F I G . 9
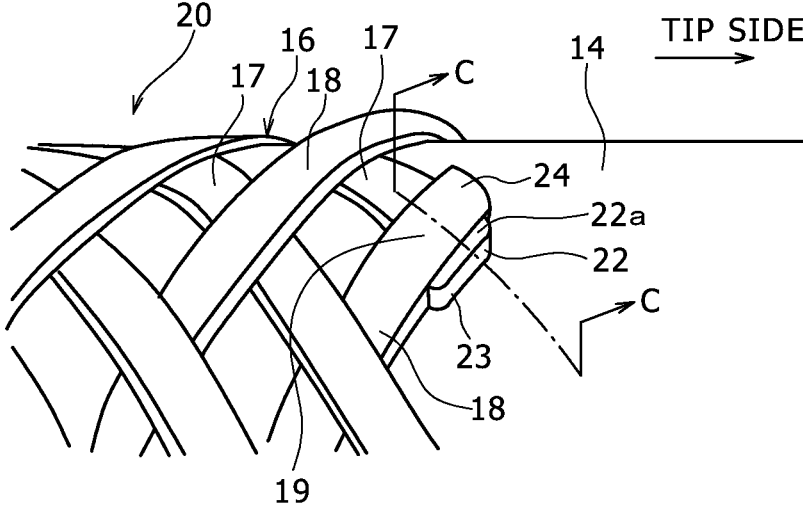
F I G . 1 0
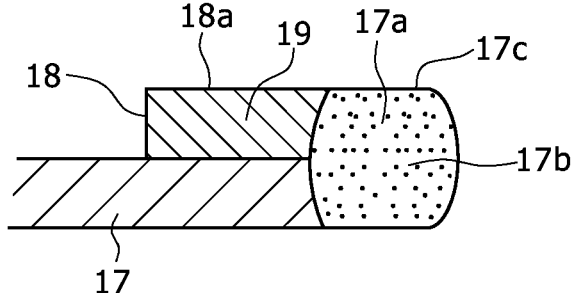
F I G . 1 1
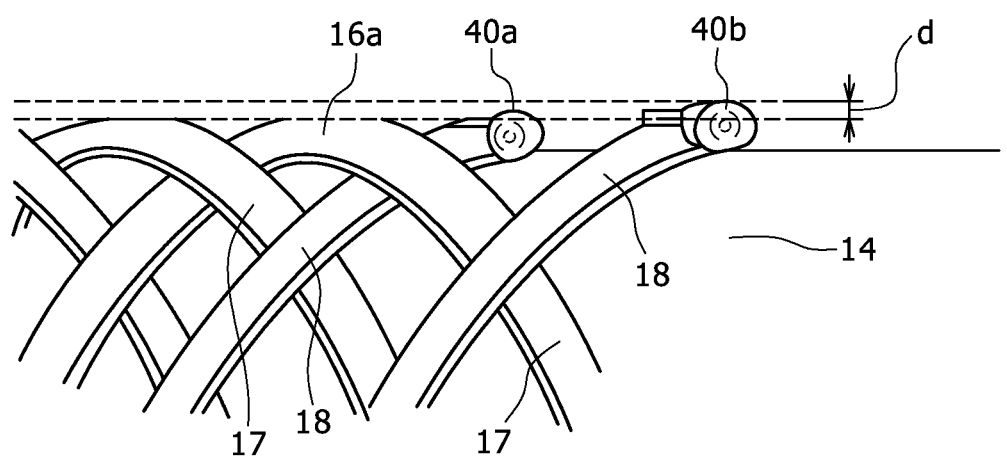

F I G . 1 6
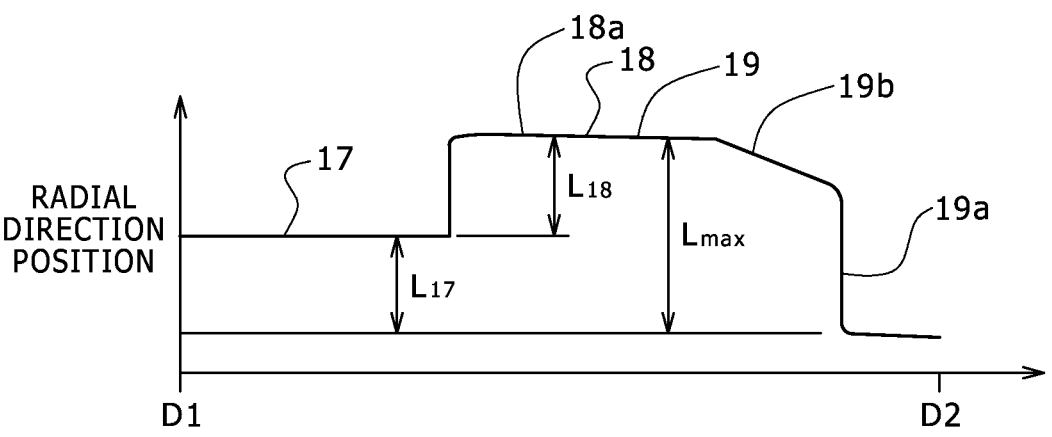
POSITION IN D1-D2 LINE DIRECTION

METHOD FOR MANUFACTURING CATHETER, AND CATHETER

CROSS REFERENCE TO RELATED APPLICATIONS

This application is a U.S. Nationalization of PCT International Application No. PCT/JP2021/044950 filed Dec. 7, 2021, which claims priority to Japanese Patent Application No. 2020-218281 filed Dec. 28, 2020, disclosure of each of which is incorporated herein, in its entirety, by this reference.

TECHNICAL FIELD

The present invention relates to a method of manufacturing a catheter and a catheter.

BACKGROUND ART

Catheters have traditionally been used for insertion into tubular organs inside the body, such as blood vessels. Catheters have a structure including an inner layer, a braided body provided on an outer circumferential side of the inner layer, and an outer layer provided on an outer circumferential side of the braided body, or a structure having a braided body provided on an inner circumferential side of an outer layer without an inner layer. The braided body functions as a reinforcement member formed by braiding metallic wires made of tungsten or stainless steel. The braided body is constituted of a plurality of first wires and a plurality of second wires crossing the first wires. After the first wires and the second wires are braided, an extra part of each wire is cut and removed to form both ends of the braided body. Patent Literature 1 describes a manufacturing method for a catheter, in which the first wires and the second wires are irradiated with laser light so as to cut the extra parts of the first wires and the second wires. Patent Literature 1 also describes that sharp residual parts, formed by cutting the extra parts, are irradiated with laser light again to form bulging parts.

CITATION LIST

Patent Literature

Patent Literature 1: JP 6080258 B

SUMMARY

Technical Problem

In a catheter manufactured by the manufacturing method disclosed in Patent Literature 1, the first wires and the second wires are irradiated with laser light to cut the extra parts. In this case, it is highly likely that the first wires and the second wires are liquefied by the heat of the laser light, and thereby rounded bulging parts are formed due to the surface tension in actuality. In the manufacturing method disclosed in Patent Literature 1, the cut parts are further irradiated with laser light to form larger bulging parts, so that a tip part of each wire may be larger in thickness than a crossing part adjacent to each tip part. When the tip part of each wire becomes larger in thickness and its radially outer end is located radially outside the crossing part, it may become necessary to increase the thickness of the outer layer so that the braided body does not protrude from the outer circumferential surface of the outer layer, or the radial direction position of the outer circumferential surface of the outer layer may be partially changed so that the outer circumferential surface of the outer layer may becomes uneven in the radial direction.

It is an advantage of the present invention to suppress, in a manufacturing method of a catheter and a catheter, a tip part of a braided body from becoming larger in thickness than a crossing part of each wire, and to suppress unevenness on the outer circumferential surface of an outer layer in the radial direction.

Solution to Problem

A manufacturing method of a catheter according to the present invention is a manufacturing method of a catheter, including a braided body having first wires and second wires crossing the first wires, and an outer layer provided on an outer circumference of the braided body. The method includes: an arranging step of arranging the braided body on a cylindrical outer circumferential surface of an inner member; a coating step of coating an outer circumferential side of the braided body with a coating member that allows laser light to pass through; a cutting step of irradiating portions of at least one of either the first wires and the second wires of the braided body with the laser light from outside of the coating member, so as to cut the one of the first wires and the second wires, the portions being located closer to a tip side than crossing parts in the braided body; and a removing step of removing the coating member from the outer circumferential side of the braided body.

According to the above configuration, it is possible to suppress the tip parts of one of the first wires and the second wires from becoming larger in thickness than the crossing parts between the first wires and the second wires due to the irradiation of laser light at the time of cutting. As a result, it becomes unnecessary to increase the thickness of the outer layer of the catheter so as to prevent the braided body from protruding from the outer circumferential surface of the outer layer, and it is also possible to suppress the unevenness on the outer circumferential surface of the outer layer in the radial direction.

In the manufacturing method of a catheter according to the present invention, in the cutting step, the portions of at least one of either the first wires and the second wires may be irradiated with the laser light from the outside of the coating member, so as to cut the one of the first wires and the second wires and to weld the first wires and the second wires, and the portions are located closer to the tip side than the crossing parts in the braided body.

According to the above configuration, it is possible to suppress the tip parts of the one of the first wires and the second wires from becoming larger in thickness than the crossing parts between the first wires and the second wires due to irradiation of laser light at the time of cutting. Moreover, it is possible to weld the first wires and the second wires concurrently with cutting the one of the first wires and the second wires. Furthermore, before cutting the first wires and the second wires by laser irradiation, it is not necessary to join the first wires and the second wires at the crossing parts in advance by laser irradiation. This makes it possible to reduce the number of times of laser irradiation.

In the manufacturing method of a catheter according to the present invention, in the cutting step, the portions of the one of either the first wires and the second wires, and the other of either the first wires and the second wires may be irradiated with the laser light from the outside of the coating member, so as to cut the one of the first wires and the second wires and to weld the first wires and the second wires, and the portions are located closer to the tip side than the crossing parts in the braided body.

According to the above configuration, it is possible to suppress the tip parts of the one of the first wires and the second wires from becoming larger in thickness than the crossing parts between the first wires and the second wires due to irradiation of laser light at the time of cutting. Moreover, after both the first wires and the second wires are melted, solidified portions can further enhance the joint strength of the first wires and the second wires.

In the manufacturing method of a catheter according to the present invention, the coating member is a combination of an inner coating part and an outer coating part that are radially overlapped and made of different materials from each other, and in the coating step, a sheet that forms the inner coating part may be laid on the inner member and the outer circumferential side of and the braided body, and then a long member, having a C-shaped radial cross section, that forms the outer coating part may be fitted with the sheet from an upper side, so as to coat the outer circumferential side of the inner member and the braided body with the coating member.

In the manufacturing method of a catheter according to the present invention, the coating member may include a shrink tube.

According to the above configuration, the coating member more easily adheres to an outer circumferential side end of the braided body, which makes it easier to suppress the tips of the one of the first wires and the second wires from becoming large in thickness due to irradiation of the laser light.

In the manufacturing method of a catheter according to the present invention, the inner member is an inner layer that forms the catheter.

According to the above configuration, when a wire material as a jig, arranged inside at the time of manufacturing, is pulled and stretched, and then pulled out from a catheter after the catheter is formed, the wire material can easily be pulled out with the presence of the inner layer, and therefore the manufacturing operation of the catheter can easily be performed.

In the manufacturing method of a catheter according to the present invention, the inner member is a jig.

According to the above configuration, since there is no need to provide an inner layer in the catheter, the cost of the catheter can be reduced by reducing the number of components.

A catheter according to the present invention includes a braided body having first wires and second wires crossing the first wires, and an outer layer provided on an outer circumference of the braid body. In the braided body, the first wires and the second wires are radially overlapped and joined at the crossing parts such that one of the first wires and the second wires are arranged radially inside the other of the first wires and the second wires, and radially outer surfaces of tip parts of the one of the first wires and the second wires, protruding to the tip side from width-directional side surfaces of portions of the other of the first wires and the second wires including the crossing parts, are arranged at identical radial direction positions on the radially outer surfaces of the other of the first wires and the second wires, or arranged radially inside at the crossing parts.

According to the above configuration, since the radially outer surfaces of the tip parts of one of the first wires and the second wires are arranged at the identical radial direction positions on the radially outer surfaces of the other of the first wires and the second wires or arranged radially inside at the crossing parts, the thickness of the tip parts of the one of the first wires and the second wires is equal to or less than the thickness of the crossing parts between the first wires and the second wires. As a result, it becomes unnecessary to increase the thickness of the outer layer of the catheter so as to prevent the braided body from protruding from the outer circumferential surface of the outer layer, and it is also possible to suppress the unevenness on the outer circumferential surface of the outer layer in the radial direction.

In the catheter according to the present invention, the first wires and the second wires may be formed by metal wires made of the same metallic material.

According to the above configuration, when the first wires and the second wires are joined by welding, the materials of the first wires and the second wires are easily melted and mixed, so that the joint strength in joint parts at the crossing parts can be enhanced.

In the catheter according to the present invention, the tip parts of the one of the first wires and the second wires may have one-side run-over parts extending so as to be away from the crossing parts along the longitudinal direction of the other of the first wires and the second wires.

According to the above configuration, the contact area between end parts of the braided body and the inner member can be increased. As a result, the end parts of the braided body are less likely to be detached from an inner layer, when the inner member is the inner layer.

In the catheter according to the present invention, the tip parts of the other of the first wires and the second wires may have other-side run-over parts running out so as to protrude from the crossing parts in a longitudinal direction of the other of the first wires and the second wires.

According to the above configuration, the contact area between the end parts of the braided body and the inner member can be increased. As a result, the end parts of the braided body are less likely to be detached from an inner layer, when the inner member is the inner layer.

A catheter according to the present invention includes a braided body having first wires and second wires crossing the first wires, and an outer layer provided on an outer circumference of the braid body. In the braided body, the first wires and the second wires are radially overlapped and joined at the crossing parts such that one of the first wires and the second wires are arranged radially inside the other of the first wires and the second wires, and the crossing parts have recess parts on tip sides of at least radially outer surfaces of the crossing parts, and the tip parts of the one of the first wires and the second wires do not protrude from tip-side lateral surfaces of the crossing parts.

According to the above configuration, since the tip parts of one of the first wires and the second wires, protruding to the tip side from the width-directional side surfaces of the other of the first wires and the second wires, are not formed, it is possible to suppress the thickness of the tip parts of the one of the first wires and the second wires from becoming larger than the thickness of the crossing parts between the first wires and the second wires. As a result, it becomes unnecessary to increase the thickness of the outer layer of the catheter so as to prevent the braided body from protruding from the outer circumferential surface of the outer layer, and it is also possible to suppress the unevenness on the outer circumferential surface of the outer layer in the radial direction.

Advantageous Effects of Invention

The manufacturing method of a catheter and a catheter according to the present invention can suppress the tip part of the braided body from becoming larger in thickness than the crossing part of each wire and to suppress unevenness on the outer circumferential surface of the outer layer in the radial direction.

BRIEF DESCRIPTION OF DRAWINGS

FIG. 1 is a view showing the state of use of a catheter as an example of an embodiment.

FIG. 3 is a perspective view showing the state where a part of an outer layer of a distal shaft is removed in the catheter shown in FIG. 2.

FIG. 8 is an enlarged view of the end part of the braided body after the wire removing step, as viewed from the outside in a radial direction.

FIG. 9 is an enlarged view of the end part of the braided body after the wire removing step, as viewed from the outside along a direction inclined with respect to a radial direction.

FIG. 10 is an enlarged C-C sectional view of FIG. 9.

FIG. 11 is a view showing that a welded part at an end part of a braided body becomes larger in a catheter in a comparative example.

FIG. 16 is a view showing an outline of a D1-D2 cross section in FIG. 15.

DESCRIPTION OF EMBODIMENTS

Hereinafter, an example of an embodiment of the present invention will be described in details with reference to the drawings. The embodiment described below is merely exemplary, and the present invention is not limited to the embodiment below.

With reference to FIGS. 1 to 10, a guide extension catheter 10 as an example of the catheter of the embodiment will be described. As shown in FIG. 1, the guide extension catheter 10 is used by, for example, inserting a leading-out part from a guiding catheter 100 into a coronary artery 102, and leading out a stent delivery catheter 106 from a distal end P of the leading-out part. In FIG. 1, the guiding catheter 100 is shown as a portion painted in black. The guide extension catheter 10 is hereinafter referred to as the catheter 10. Since the catheter 10 is used in the state as shown in FIG. 1, its distal end P is required to be flexible so as to facilitate insertion into organs such as blood vessels.

Figure 2:
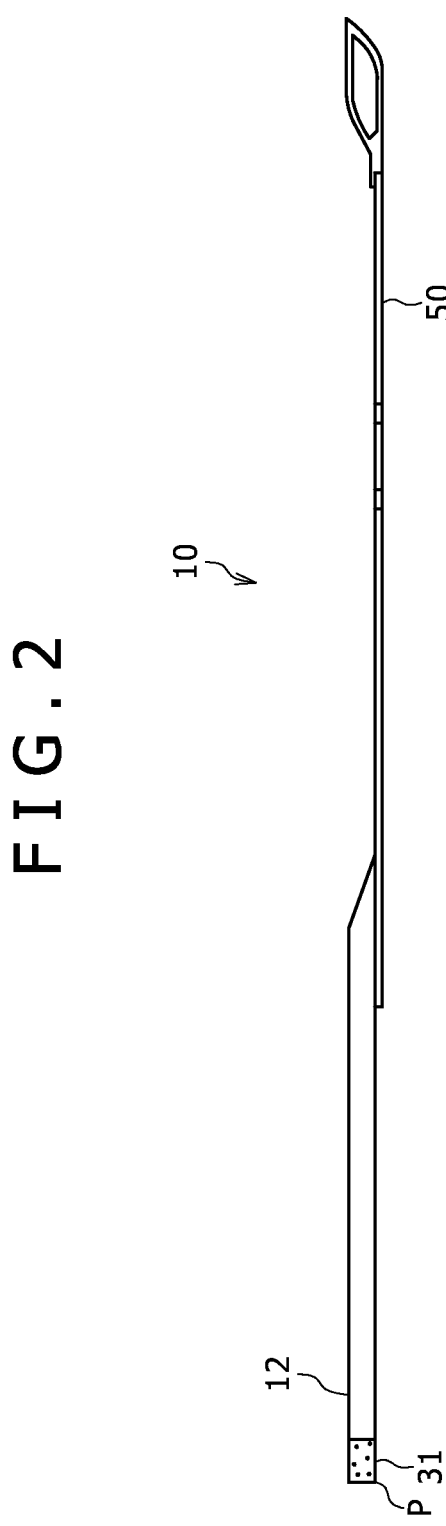
FIG. 2 is an overall view of the catheter shown in FIG. 1.

FIG. 2 is an overall view of the catheter 10. The catheter 10 is a long member configured by including a cylindrical distal shaft 12 and a proximal shaft 50 which is connected to a proximal end part of the distal shaft 12 and is made of a metal wire. The distal end of the proximal shaft 50 is connected to a part of the outer circumferential surface of the distal shaft 12 in a circumferential direction. In the present embodiment, the "proximal end side" refers to a rear side (right side in FIG. 2) in the direction in which the catheter 10 is inserted into a blood vessel. The "distal end side" refers to a front side (left side in FIG. 2) in the direction in which the catheter 10 is inserted into the blood vessel.

Figure 4:
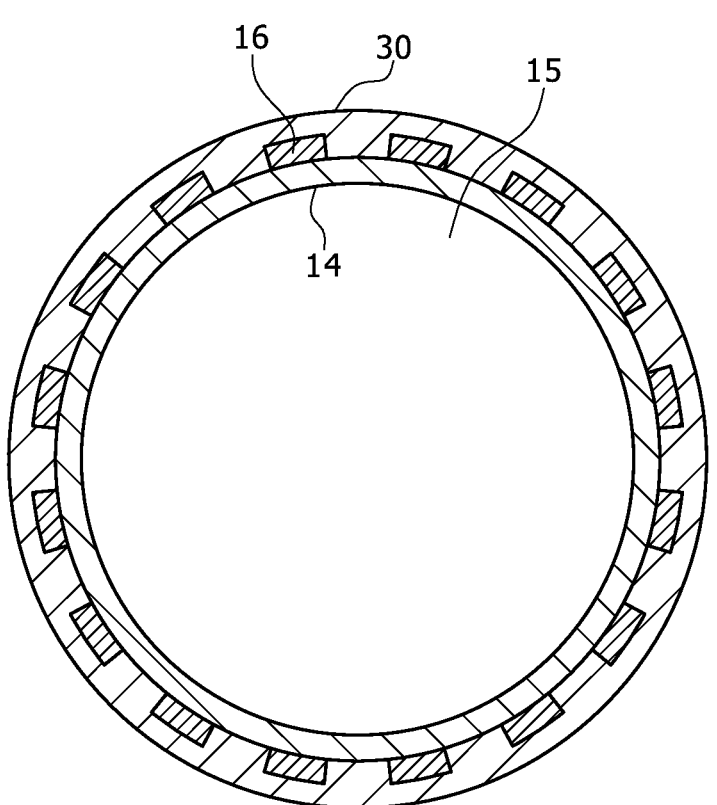
FIG. 4 is a schematic A-A sectional view of FIG. 3.

FIG. 3 is a perspective view showing the state where a part of an outer layer 30 of the distal shaft 12 is removed in the catheter 10. FIG. 4 is a schematic A-A sectional view of FIG. 3. The distal shaft 12 includes an inner layer 14 made of resin, a braided body 16 provided on the outer circumference of the inner layer 14, and the outer layer 30 provided on the outer circumference of the braided body 16, the outer layer 30 having resin. The inner layer 14 corresponds to the inner member and forms the catheter 10.

The inner layer 14 forms a lumen 15 into which other catheters are inserted. The resin material that constitutes the inner layer 14 is not particularly limited, and may include polytetrafluoroethylene (PTFE), for example. The inner layer 14 is not limited to a single-layer tube, and may be a multilayer tube made of identical or different materials.

The braided body 16 is formed by braiding first wires 17 and second wires 18 in a mesh shape. For example, the plurality of first wires 17 are wound around the outside of the inner layer 14 along a first direction inclined with respect to a longitudinal axis of the distal shaft 12. The plurality of second wires 18 are wound around the outside of the inner layer 14 along a second direction inclined with respect to the longitudinal axis of the distal shaft 12 and crossing the first direction. The first wires 17 and the second wires 18 are formed by metal wires made of the same metallic material, such as tungsten, or stainless steel. FIG. 4 schematically shows the cross section of the braided body 16 with a plurality of rectangle parts. While the shapes of radial cross sections of the first wires 17 and the second wires 18, which are orthogonal to their respective longitudinal directions, are rectangular, the shapes of radial cross sections of one of or both the first wires 17 and the second wires 18 may be circular. FIG. 4 shows portions of the first wires 17 and the second wires 18 overlapped at the respective crossing parts as the braided body 16.

The outer layer 30 covers the outer circumference of the inner layer 14 and the braided body 16. Hence, the outer layer 30 is provided on the outer circumference of the braided body 16. Resin materials constituting the outer layer 30 are not particularly limited, and the outer layer may be formed by, for example, polyether block amide (PEBA), polyethylene (PE), polypropylene (PP), polyamide (PA), polyimide (PI), polyamideimide (PAI), polyethylene terephthalate (PET), polyurethane (PU), nylon elastomer, polyester elastomer, ethylene-vinyl acetate resin (EVA), polyvinyl chloride (PVC), etc. For example, Pebax (registered trademark) made by Arkema Inc. may be used as resin constituting the outer layer 30. An outer circumferential surface of the outer layer 30 may preferably be coated with a hydro-philic coat, such as hyaluronic acid, polyvinylpyrrolidone (PVP), polyvinyl alcohol (PVA), polyvinyl alkyl ether, and maleic anhydride copolymer (VEMA). For example, the hydrophilic coat may be applied only to a portion of the outer layer 30 that is from the distal end P to a prescribed position in a longitudinal intermediate part. The outer layer 30 is not limited to a single-layer tube, and may be a multilayer tube made of identical or different materials. The outer layer 30 may also have different hardness in a plurality of portions in the longitudinal direction. For example, when the outer layer 30 is divided into a distal end part, an intermediate part, and a proximal end part, the resin forming the distal end part may have a lowest hardness, the resin forming the proximal end part may have a highest hardness, and the resin forming the intermediate part may have a hardness between the hardness of the resin in the distal end part and in the proximal end part.

In addition, the distal end part of the distal shaft 12 is provided with a tip chip 31 (FIG. 2), which is formed from a part of the outer layer and made of resin with X-ray opaque metal powder mixed therein. In FIG. 2, the tip chip 31 is expressed with a sand hatching pattern at the tip part of the distal shaft 12. Examples of the metal powder to be used include bismuth oxide (Bi), tungsten (W), and barium sul-fate. Since the tip chip 31 is constituted by mixing the X-ray opaque metal powder into the resin of the outer layer 30, the flexibility of the tip part of the distal shaft 12 is secured, while an operator easily recognizes the distal end position of the distal shaft 12 under X-ray fluoroscopy.

Furthermore, by arranging the braided body 16 in an area other than a range from the distal end of the distal shaft 12 to a prescribed length, the distal end of the distal shaft 12 is made more flexible and the catheter 10 is more easily inserted into tubular organs such as blood vessels. In order to form the braided body 16 in this way, an extra part of the braided body 16, located at the distal end side of the distal shaft 12, is cut and removed by laser irradiation, and the tip parts of the first wires 17 and the second wires 18 in a cut part are welded to each other so as to prevent the braided body 16 from being unbraided through the cut portions. Hereinafter, description will mainly be given of the tip part of the braided body 16 located on the distal end side of the distal shaft 12.

At the tip part of the braided body 16 that is located on the distal end side of the distal shaft 12, the first wires 17 and the second wires 18 are radially overlapped and joined by welding at crossing parts 19 such that one of either the first wires 17 and the second wires 18 are arranged radially inside the other of the wires, and tip parts 22 (FIG. 7) of the one of the wires protrude to the tip side from width-directional side surfaces of the portions of the other of the wires, including the crossing parts. Furthermore, radially outer surfaces 22a (FIG. 7) of the tip parts 22 of the one of the wires are arranged at identical radial direction positions on the radially outer surfaces of the other of the wires or arranged radially inside at the crossing parts 19. As a result, it is possible to suppress the tip parts 22 of the one of the wires from becoming larger in thickness than the crossing parts 19. Therefore, it becomes unnecessary to increase the thickness of the outer layer 30 so as to prevent the braided body 16 from protruding from the outer circumferential surface of the outer layer 30, and it is also possible to suppress the unevenness on the outer circumferential surface of the outer layer 30 in the radial direction.

In addition, the first wires 17 and the second wires 18 are formed by metal wires made of the same metallic material, and therefore when the first wires and the second wires are joined by welding as in this example, the materials of the first wires and the second wires are easily melted and mixed. As a result, the joint strength of joint parts at the crossing parts 19 between the first wires 17 and the second wires 18 can be enhanced.

As shown in FIGS. 8 and 9 described later, the tip parts 22 of one of the wires have one-side run-over parts 23 extending along a longitudinal direction of the other of the wires so as to be away from the crossing parts. This makes it possible to increase the contact area between the end parts of the braided body 16 and the inner layer 14, so that the end parts of the braided body 16 are less likely to be detached from the inner layer 14.

Next, a manufacturing method of the catheter 10 will be described with reference to FIGS. 5A to 10. First, an "arranging step" is performed to arrange the braided body 16 on a cylindrical outer circumferential surface that is the outer circumferential surface of the inner layer 14. At this time, the inner layer 14 may be formed into a long cylin-drical shape on a metal core line or on a shaft portion formed on the jig by extrusion molding with a resin material extruder or the like. To arrange the braided body 16 on the outer circumference of the inner layer 14, a braiding machine may be used. The braiding machine winds the plurality of first wires 17 around the cylindrical outer circumferential surface of the inner layer 14 along the first direction inclined with respect to the longitudinal axis of the inner layer 14, and winds the plurality of the second wires 18 in the second direction that is inclined with respect to the longitudinal axis of the inner layer 14 and that is crossing the first direction. In this case, the braided body 16 is arranged so as to extend almost to the tip of the inner layer 14.

Figure 5A:
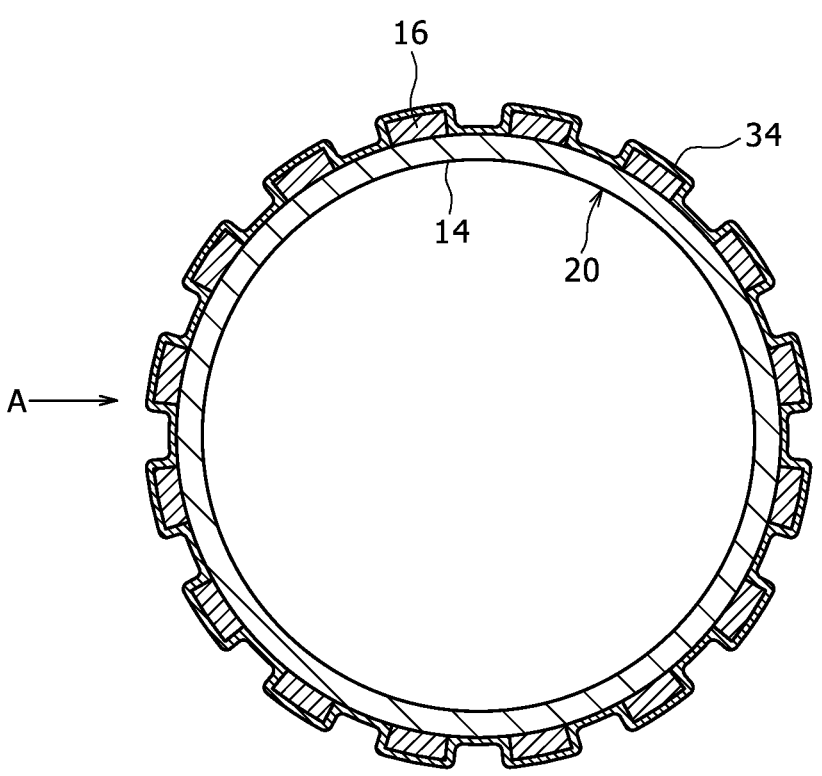
FIG. 5A is a sectional view corresponding to FIG. 4, in which a braided body is arranged on an outer circumference of an inner layer and is coated with a coating member from the above.
Figure 5B:
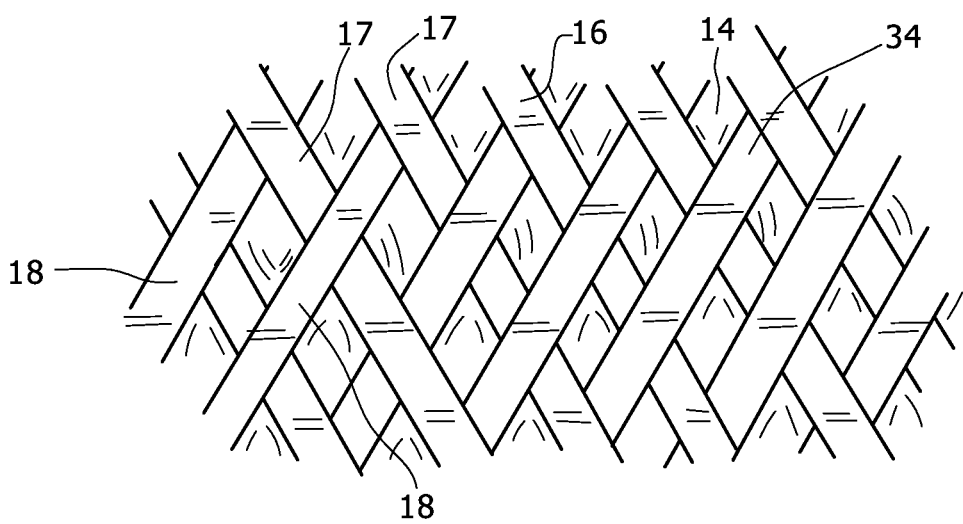
FIG. 5B is a view as viewed in the direction of arrow A in FIG. 5A.

Next, a "coating step" is performed. In the coating step, as shown in FIGS. 5A and 5B, the outer circumferential side of the braided body 16 is coated with a transparent or translucent coating member 34 that allows laser light to pass through, in an intermediate member 20 (FIG. 5A) consti-tuted of the inner layer 14 and the braided body 16. For example, a transparent shrink tube is used as the coating member 34. The shrink tube has a function of reducing in diameter as a result of heating. The shrink tube is formed by resin materials such as FEP (a fluororesin that is a copolymer of tetrafluoroethylene and hexafluoropropylene). The shrink tube is heated up to a shrinkage temperature of the shrink tube by a heater or with high-frequency electromagnetic waves, in the state of covering the outer circumferential side of the intermediate member 20, and presses the outer cir-cumference of the braided body 16. In the illustration of FIG. 5A, the coating member 34 adheres to the outer circumference surface of the inner layer 14, but the coating member 34 may be in a generally cylindrical shape so as to adhere only to an outermost circumferential surface of the braided body 16.

Figure 6:
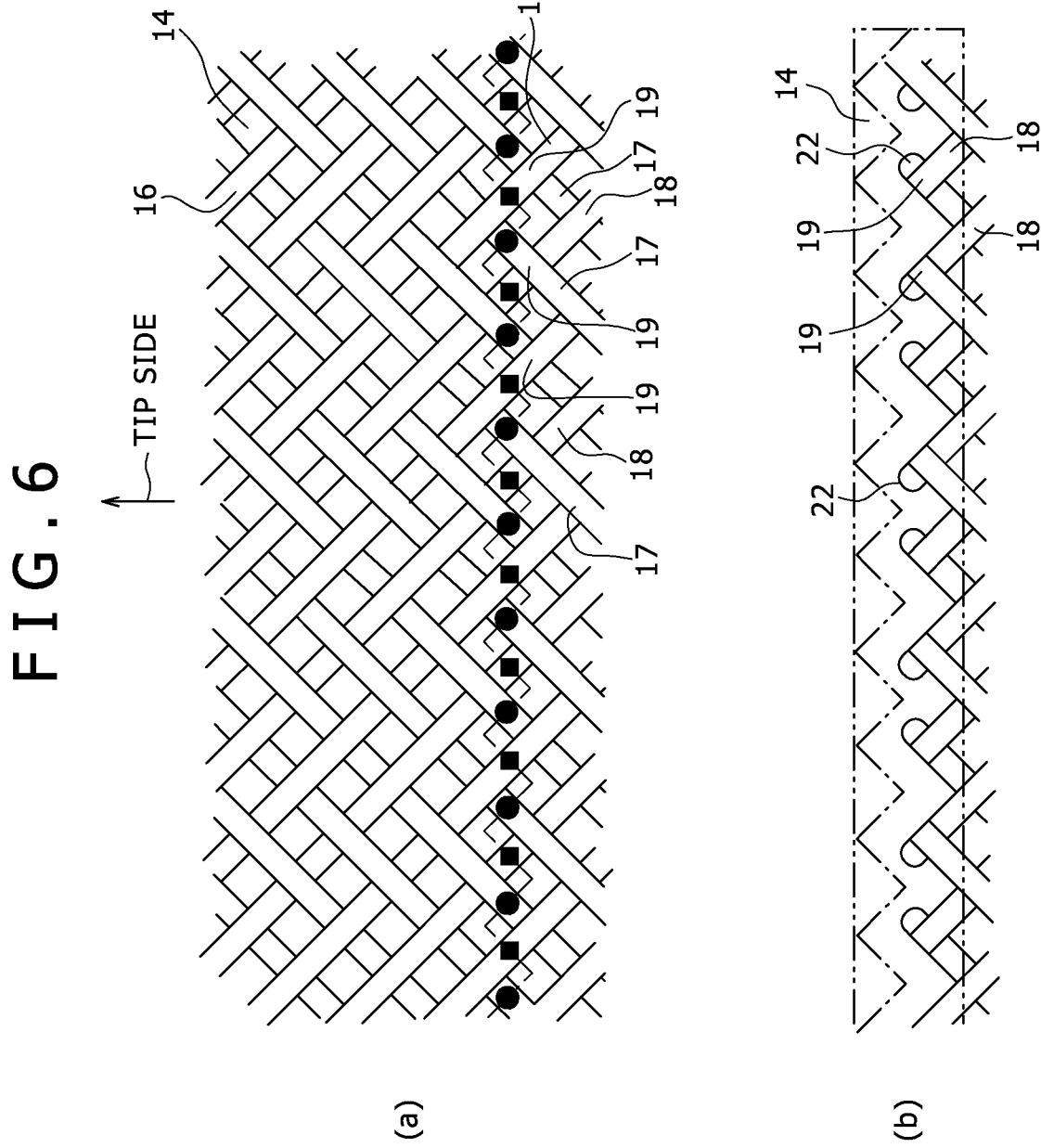
FIG. 6(a) is a view showing a cutting line when an end part of the braided body is cut with laser light.
FIG. 6(b) is a view showing the end part of the braided body after cutting, in a manufacturing method of a catheter in the embodiment.

Then, a "cutting step" is performed. FIG. 6(a) is a view showing a cutting line when the end part of the braided body 16 is cut with laser light, and FIG. 6(b) is a view showing the end part of the braided body 16 after cutting. In FIG. 6, black circles indicate portions of the first wires 17 irradiated with laser light, and black squares indicate portions of the second wires 18 irradiated with laser light. In FIG. 6, illustration of the coating member 34 is omitted. When the black circle portions and the black square portions are irradiated with laser light, the portions of the first wires 17 and the second wires 18 irradiated with the laser light are melted, and each of the wires 17 and 18 are cut by this melting. At this time, with the cutting of each of the wires 17 and 18, a melting part of a portion of the wire arranged on the inner circumferential side at the crossing part 19 between two wires 17 and 18, which extend from the crossing part 19, comes closer to the crossing part 19 and solidifies, so that the first wire 17 and the second wire 18 are joined. The portion of solidified melting part forms the tip part 22 of the wire arranged on the inner circumferential side, the tip part 22 protruding from the crossing part 19 toward the tip side. Note that the melting part of a portion of the wire arranged on the outer circumferential side at the crossing part 19, which extends from the crossing part 19, may come closer to the crossing part 19 and solidify. However, FIG. 6(b) omits illustration of the tip part of the wire arranged on the outer circumferential side, the tip part being formed by the portion of solidified melting part.

More specifically, portions of at least one of the first wires 17 and the second wires 18 in the braided body 16, located closer to the tip side than the crossing parts 19, are irradiated with the laser light from the outside of the coating member 34. Then, the one of the wires is cut, while the first wires 17 and the second wires 18 are welded.

Figure 7:
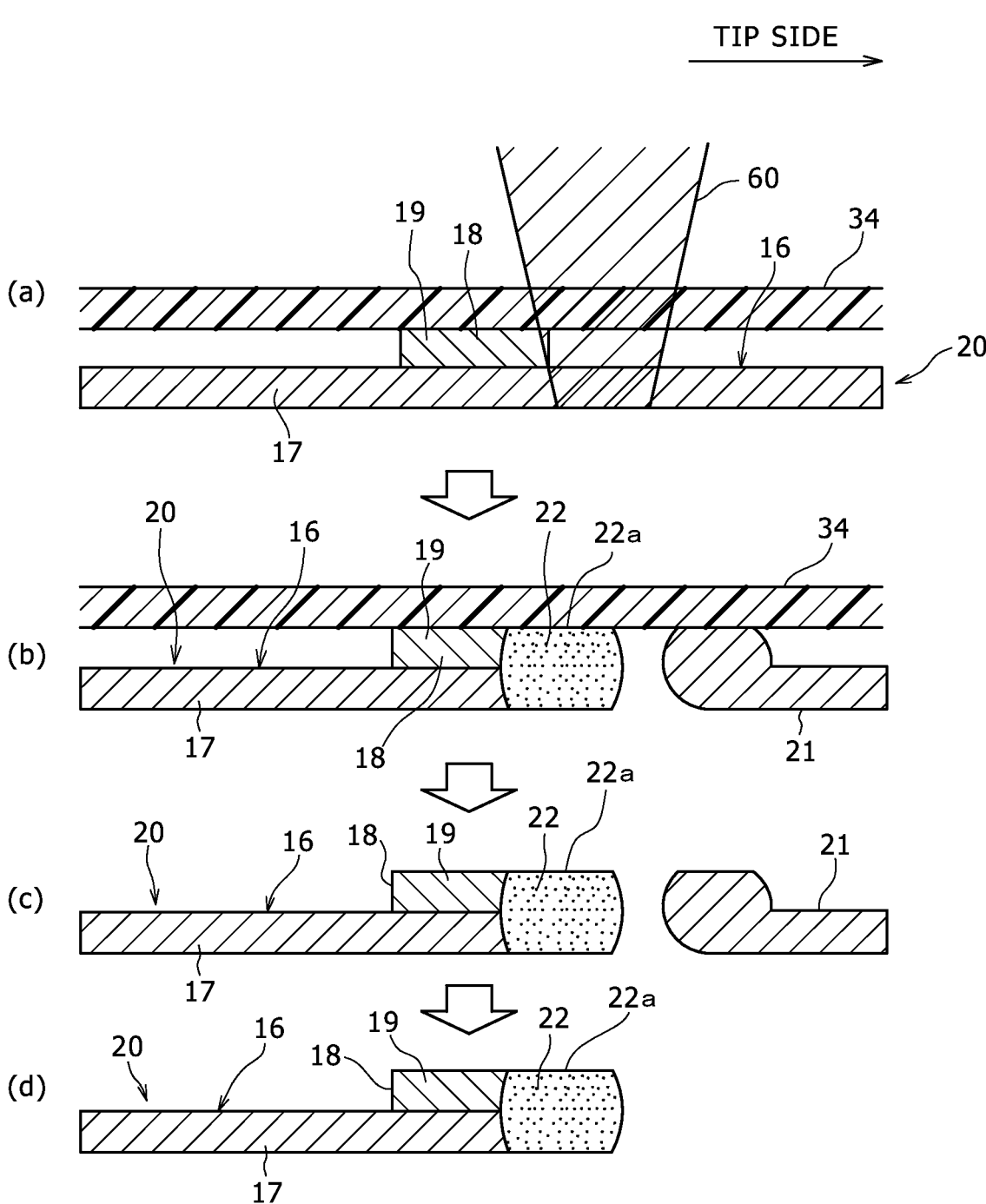
FIG. 7 is a view showing a cutting step of irradiating the braided body with laser light to cut first wires, a coating removing step of removing the coating member, and a wire removing step of removing extra parts of the first wires in the manufacturing method of a catheter in the embodiment.

FIG. 7 shows cutting steps (a) and (b) in which the first wires 17 of the braided body 16 are irradiated with laser light 60 to cut the first wires 17, a coating removing step (C) to remove the coating member 34, and a wire removing step (d) to remove extra parts of the first wires 17.

As shown in FIG. 7(a), laser light 60 passes through the coating member 34 and is applied to a portion of the tip part of the first wire 17, which is located closer to the tip side than the crossing part 19 between the first wire 17 and the second wire 18. In this case, the first wire 17 passes through the inner circumferential side of the second wire 18 at the crossing part 19. The laser light 60 is also partially applied to the second wire 18 at the crossing part 19.

As shown in FIG. 7(b), with irradiation of laser light, a portion of the first wire 17, which passes through the inner circumferential side of the second wire 18 at the crossing part 19 and locates on the tip side from the side surface of the second wire 18, is cut away from a portion of the first wire 17 closer to the tip side. At the same time, the melted part of the first wire 17 becomes larger in thickness in a radial direction as it is deformed so as to be closer to the crossing part 19, or the like, and the tip part 22 of the first wire 17 protruding to the tip side than the crossing part 19 is formed. The tip part 22 of the first wire 17 and the portion of the second wire 18 located at the crossing part 19 are joined by welding. In FIG. 7(b), the tip part 22 of the first wire 17 is indicated by a sand hatching pattern. At the tip part 22 of the first wire 17, the melted portion of the second wire 18 may be mixed with the melted portion of the first wire 17 and solidified. In this specification, for each wire to be joined at the crossing part 19, a portion which is closer to the tip side than the crossing part 19 and located on an extension line of each wire is referred to as the tip part of the wire, regardless of whether the melted portion of each wire is mixed or not. In addition, the outer circumferential side of the braided body 16 is pressed by the coating member 34.

Furthermore, although not shown in FIG. 7, in the cutting step, the second wire 18 in the braided body 16, which extends to the tip side from the crossing part where the second wire 18 is arranged on the inner circumferential side of the first wire 17, is irradiated with laser light, so that the second wire 18 is cut, while the first wire 17 and the second wire 18 are welded. The situation in this case is similar to the situation in which the first wire 17 and the second wire 18 in FIG. 7 are reversed. In this case, the laser light 60 passes through the coating member 34 and is applied to a portion of the tip part of the second wire 18, which is located closer to the tip side than the crossing part between the first wire 17 and the second wire 18. The laser light 60 is also partially applied to the first wire 17 at the crossing part. Thus, in the cutting step, portions of one of either the first wires 17 and the second wires 18 in the braided body 16, located closer to the tip side than the crossing parts 19, and the other of the wires, are irradiated with the laser light from the outside of the coating member 34, so as to cut the one of the wires while welding the first wires 17 and the second wires 18. When the portions of one of either the first wires 17 or the second wires 18, located closer to the tip side than the crossing parts, are irradiated with laser light, the one of the wires may be cut, while the first wires 17 and the second wires 18 may be welded without irradiation of the other of either the wires with laser light.

Next, as shown in FIG. 7(c), the coating removing step is performed to remove the coating member 34 from the outer circumferential side of the braided body 16 and the inner layer 14, and then a wire removing step (FIG. 7(d)) is performed to remove extra parts 21 that are separated from the braided body 16 at the cut part of the first wires 17.

FIG. 8 is an enlarged view of the end part of the braided body 16 after the wire removing step, as viewed from the outside in a radial direction. FIG. 9 is an enlarged view of the end part of the braided body 16 after the wire removing step, as viewed from the outside along a direction inclined with respect to the radial direction. FIG. 10 is an enlarged C-C sectional view of FIG. 9. As shown in FIGS. 8 to 10, in the state after the wire removing step, the tip parts 22 of the first wires 17 protruding from the tip-side lateral surfaces of the second wires 18 are each formed at the end part of the braided body 16. Then, using the tip parts 22 of the first wires 17, the first wires 17 and the second wires 18 are joined at the plurality of crossing parts 19. At this time, since the outer circumferential side of the braided body 16 is coated with the coating member 34 in the cutting step as described above, the radially outer surfaces 22a of the tip parts 22 of the first wires are also pressed by the coating member 34. Accordingly, the radially outer surfaces 22a of the tip parts 22 of the first wires 17 (one of the wires) are arranged at the same radial direction (up-down direction in FIG. 10) positions on the radially outer surfaces 18a (FIG. 10) of the second wires 18 (the other of the wires), or radially inside (lower side in FIG. 10) at the crossing parts 19. In addition, the radially outer surfaces 22a of the tip parts 22 of the first wires are flat surfaces. Although illustration is omitted in FIGS. 8 to 10, tip parts of the second wires 18 located on the inner circumferential side are also formed at the end part of the braided body 16 in the state after the wire removing step, these tip parts protruding from the tip-side lateral surfaces of the first wires 17 located on the outer circumferential side. The tip parts of the second wires 18 have the similar form as the tip parts 22 of the first wires 17, protruding from the tip-side lateral surfaces of the second wires 18.

Furthermore, as shown in FIGS. 8 and 9, the tip parts 22 of one of the wires (the first wires 17) on the inner circumferential side have one-side run-over parts 23 extending so as to be away from the crossing parts 19, along the longitudinal direction of the other of the wires (second wires 18) on the outer circumferential side. In FIGS. 8 and 9, the one-side run-over part 23 is shown in an exaggerated manner. The reason why the one-side run-over parts 23 are formed in this way is as follows. That is, when the braided body 16 is irradiated with the laser light 60, the outer circumferential side of the braided body 16 is coated with the coating member 34, and the radially outer surfaces 22*a* of the tip parts 22 of one of the wires are pressed by the coating member 34. When the melted tip parts of the first wires 17 come closer to the crossing parts 19 due to the irradiation of the laser light, the portions unable to escape radially outward extend so as to escape in the circumferential direction. In the example shown in FIG. 8, at portions of the other of the wires (second wires 18) adjacent to the crossing parts 19, the other-side run-over parts 24 are also formed, running over so as to protrude from the crossing parts 19 in the longitudinal direction of the other of the wires. The respective one-side run-over parts 23 and the other-side run-over parts 24 can increase the contact area between the end part of the braided body 16 and the inner layer 14. As a result, the end part of the braided body 16 is less likely to be detached from the inner layer 14.

After the wire removing step in FIG. 7(*d*), the outer layer 30 made of resin is molded on the outer circumferential side of the intermediate member 20 to form the distal shaft 12. Then, the distal shaft 12 is coupled to the proximal shaft 50 to form the catheter 10.

According to the above manufacturing method of the catheter 10, it is possible to suppress an increase in thickness of the tip parts of one of the wires due to irradiation of laser light 60 at the time of cutting. Furthermore, before cutting the first wires 17 and the second wires 18 by laser irradiation, it is not necessary to join the first wires 17 and the second wires 18 at the crossing parts 19 in advance by laser irradiation. This makes it possible to reduce the number of times laser irradiation is performed.

Furthermore, in the cutting step, portions of one of either the first wires 17 and the second wires 18 in the braided body 16, located closer to the tip side than the crossing parts 19, and the other of the wires, are irradiated with the laser light 60 from the outside of the coating member 34, so as to cut the one of wires while welding the first wires 17 and second wires 18. As a result, after both the first wires 17 and the second wires 18 are melted, solidified portions can further enhance the joint strength of the first wires 17 and the second wires 18. In addition, when a shrink tube is used as the coating member 34, the coating member 34 more easily adheres to the outer circumferential side end of the braided body 16, which makes it easier to suppress an increase in thickness of the tips of the one of the wires due to irradiation of the laser light. In addition, the inner member arranged on the inner circumferential side of the braided body 16 is used as the inner layer 14 that forms the catheter 10, and therefore, when a wire material as a jig, arranged inside at the time of manufacturing, is pulled and stretched, and then pulled out from the catheter 10 after the catheter 10 is formed, the wire material can be easily pulled out with the presence of the inner layer 14. Therefore the manufacturing operation of the catheter 10 can be easily performed.

Moreover, according to the aforementioned catheter 10, in the braided body 16, the first wires 17 and the second wires 18 are radially overlapped and joined at the crossing parts 19 such that the one of the first wires and the second wires is arranged radially inside the other of the wires, and the radially outer surfaces 22*a* of the tip parts 22 of the one of the wires, protruding to the tip side from the width-directional side surfaces of the portions of the other of the wires including the crossing parts, are respectively arranged at the same radial direction positions on the radially outer surfaces of the other of the wires, or arranged radially inside at the crossing parts 19. As a result, the thickness of the tip parts of the one of the wires becomes equal to or less than the thickness of the crossing parts 19. Therefore, it becomes unnecessary to increase the thickness of the outer layer 30 of the catheter 10 so as to prevent the braided body 16 from protruding from the outer circumferential surface of the outer layer 30, and it is also possible to suppress the unevenness on the outer circumferential surface of the outer layer 30 in the radial direction. Note that description has been given of the case where the thickness of the tip parts 22 of one of the wires arranged radially inside at the crossing parts 19 is equal to or less than the thickness of the crossing parts 19. On the other hand, the tip parts of the other of the wires arranged radially outside at the crossing parts 19, protruding from the crossing parts 19, also have a thickness that is equal to or less than the thickness of the crossing parts 19, and the radially outer surfaces of the tip parts of the other of the wires are arranged at identical radial direction positions on the radially outer surfaces of the other of the wires, or are arranged radially inside at the crossing parts 19.

FIG. 11 is a view showing that a welded part at a tip part of a braided body 16*a* becomes larger in a catheter in a comparative example. In the catheter in the comparative example having a configuration different from that shown in FIGS. 1 to 10, the braided body 16*a* is irradiated with laser light so as to cut the first wires 17 and the second wires 18, and when the first wires 17 and the second wires 18 are welded, the outer circumferential side of the inner layer 14 and the braided body 16*a* are not covered with a coating member in advance. FIG. 11 shows that at portions of the first wires 17 passing through the inner circumferential side of the second wires 18 and being located on the tip side from the side surfaces of the second wires 18, joint parts 40*a*, 40*b* having swelling parts swelling toward radially outside are formed by irradiation of the laser light, and with the joint parts 40*a* and 40*b*, the first wires 17 and the second wires 18 are welded. At the time of such welding of the first wires 17 and the second wires 18, the joint parts 40*a* and 40*b* bulge radially outside with their radially outer surfaces not pressed by the coating member. In the state of FIG. 11, the joint parts 40*a* and 40*b* bulge more radially outward than an outermost circumferential surface of the braided body 16*a* except for the tip parts of the first wires 17 and the second wires 18, and the radially outer ends of the joint parts 40*a* are located outside the aforementioned outermost circumferential surface by a radial distance d (for example, about a few tens of μm). In the catheter in such a comparative example, the joint parts 40*a* and 40*b* that are the tip parts of the first wires 17 and the second wires 18 are larger in thickness than the crossing parts adjacent to its joint parts. Therefore, it may become necessary to increase the thickness of the outer layer that coats the outer circumferential side of the braided body 16, so that the braided body 16*a* does not protrude from the outer circumferential surface of the outer layer, and the radial direction position of the outer circumferential surface of the outer layer may not partially change, resulting in the outer circumferential surface of the outer layer becoming uneven in the radial direction. According to the embodiment shown in FIGS. 1 to 10, such inconvenience can be prevented.

Figure 12:
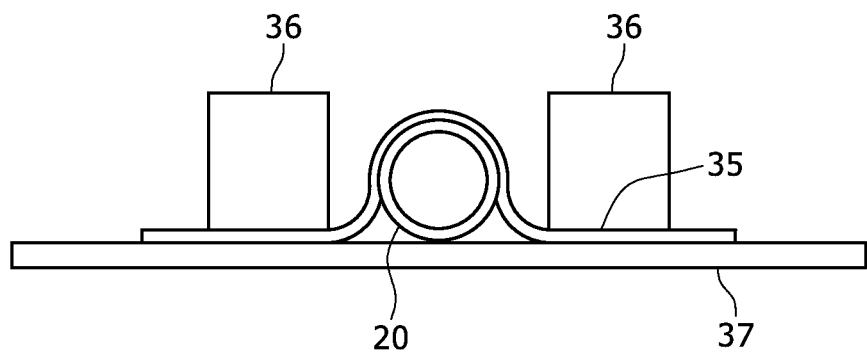
FIG. 12 is a view showing a coating step in a manufacturing method of a catheter in another example of the embodiment.

FIG. 12 is a view showing a coating step in a manufacturing method of a catheter in another example of the embodiment. For the coating step in the manufacturing method of this example, a sheet 35 made of silicone rubber with a very small thickness (for example, about 100 μm thick) is used as the coating member, instead of the shrink tube. The sheet 35 is translucent and non-adhesive. In the coating step, a width-directional (right-left direction in FIG. 14) intermediate part of the sheet 35 is laid on the outer circumferential side of a portion of the intermediate member 20, constituted by the inner layer 14 and the braided body 16, including a portion to be welded of the braided body 16 (FIG. 3). Then, block-shaped magnets 36 are respectively arranged on the upper side of both width-directional end parts of the sheet 35, and both end parts of the sheet 35 are fixed to a plate 37 which is made of a magnetic material, such as iron plate, and arranged on the top surface of a fixing base, using magnetic force acting between the top surface of the plate 37 and the magnets 36. The welding step is performed in this state. For example, in the cutting step, an area round a cutting planned part is irradiated with laser light from the upper side of the intermediate member 20, while the intermediate member 20 is rotated little by little. In the manufacturing method in this example, the other configurational aspects are similar to those in FIGS. 1 to 10.

Figure 13:
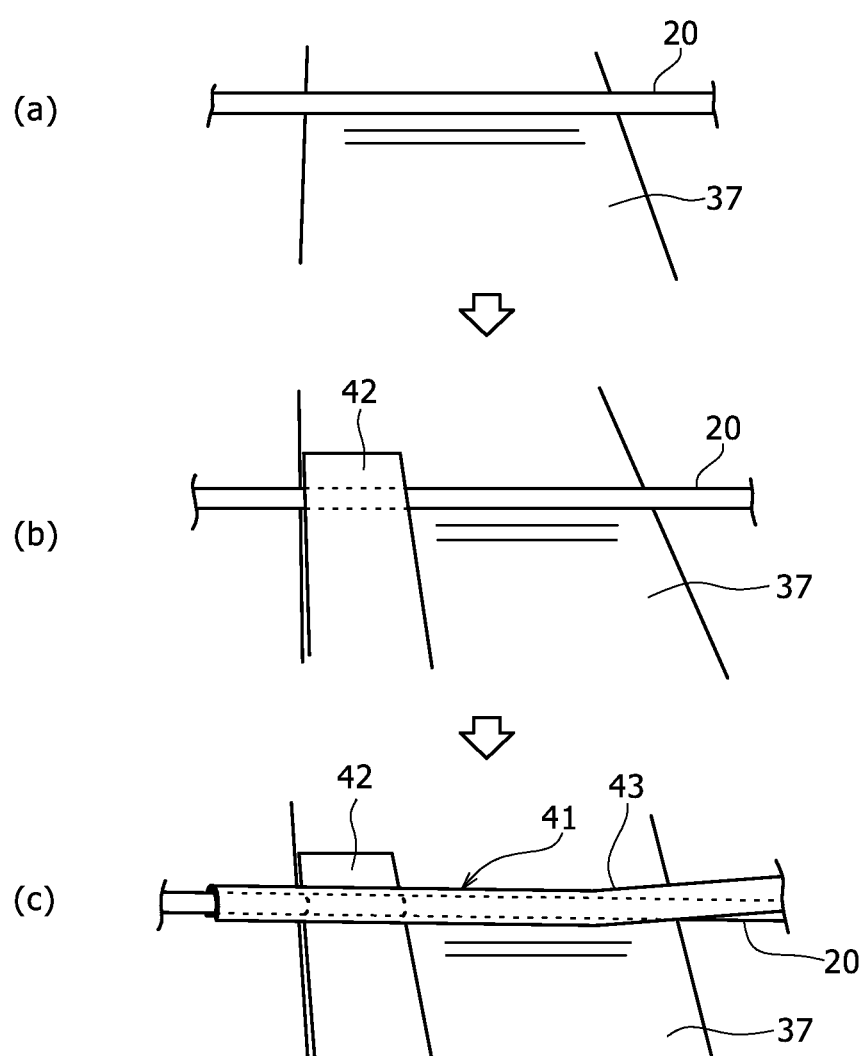
FIG. 13 is a view showing the coating step in the manufacturing method of a catheter in another example of the embodiment.
Figure 14:
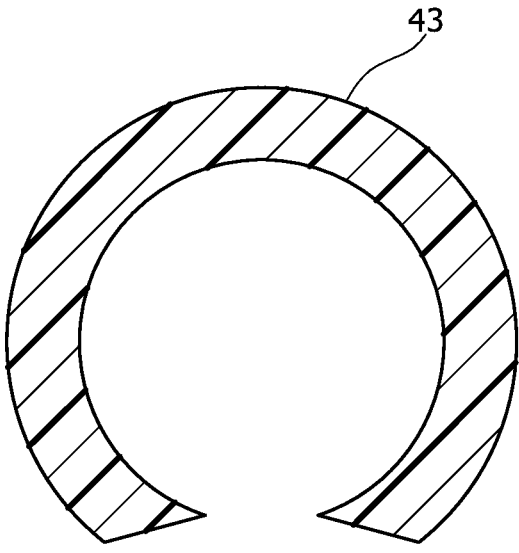
FIG. 14 is a radial sectional view of an outer coating part of a coating member used in the manufacturing method shown in FIG. 13.

FIG. 13 is a view showing the coating step in the manufacturing method of the catheter in another example of the embodiment. FIG. 14 is a sectional view showing an outer coating part 43 of a coating member 41 used in the manufacturing method shown in FIG. 13. In the manufacturing method in this example, a combination of an inner coating part 42 and the outer coating part 43 is used as the coating member 41, the inner coating part 42 and the outer coating part 43 being radially overlapped with each other and made of different materials from each other, with the outer coating part 43 being on the outer circumferential side of the inner coating part 42. The inner coating part 42 is formed from, for example, a sheet made of silicone rubber with a very small thickness, similar to the sheet 35 shown in FIG. 12. For the outer coating part 43, a long member having a C-shaped radial cross section is used, for example. The outer coating part 43 is formed by, for example, fitting a shrink tube to a long axial member, causing the shrink tube to thermally shrink, and then removing a part of the shrink tube in the circumferential direction over the entire longitudinal length.

In the coating step, the outer side of the braided body 16 (FIG. 3) is coated with the coating member 41. In the coating step, as shown in FIG. 13(a), on the top surface of the plate 37 made of a magnetic material, such as iron plate, and placed on the fixing base, the intermediate member 20 is arranged in the state of being gripped at its longitudinal end parts by jigs (not shown). Then, as shown in FIG. 13(b), a longitudinal (up-down direction in FIGS. 13(b) and 13(c)) intermediate part of the inner coating part 42 is laid on the outer circumferential side of a portion of the intermediate member 20, the portion including the portion to be welded of the braided body 16. Then, as shown in FIG. 13(c), the outer coating part 43 is fitted to a portion of the inner coating part 42, including an arrangement part of the intermediate member 20, from above the inner coating part 42. As a result, the outer circumferential side of the inner layer 14 (FIG. 3) and the braided body 16 can be coated with the coating member 41, and the outer circumferential side end of the braided body 16 can be pressed by the coating member 41. The cutting step is performed in the state where both the longitudinal end parts of the inner coating part 42, which extend outside the outer coating part 43, are fixed to the plate 37 by the magnetic force of the magnets 36, or the like, shown in FIG. 12, for example. In the manufacturing method in this example, the other configurational aspects are similar to those in FIGS. 1 to 10 or those in FIG. 12.

Figure 15:
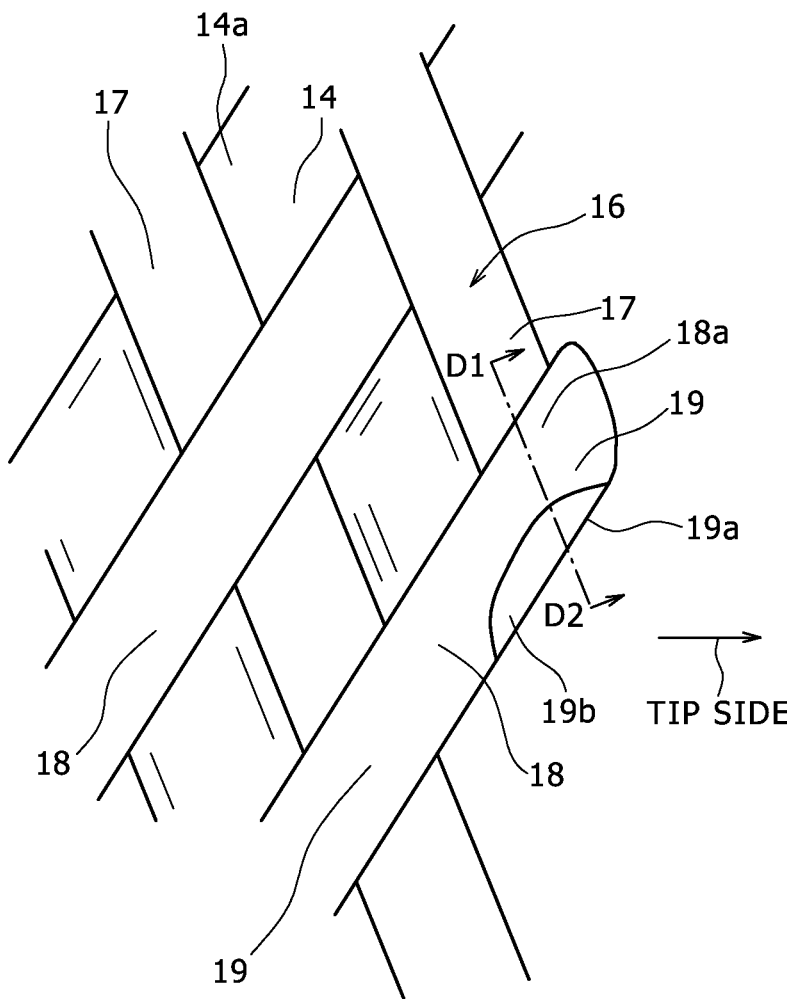
FIG. 15 is a view of a catheter in another example of the embodiment, corresponding to FIG. 8.

FIG. 15 is a view of a catheter in another example of the embodiment, corresponding to FIG. 8. FIG. 16 is a view showing an outline of a D1-D2 cross section in FIG. 15. In the case of the catheter in this example, as in each example shown above, the first wires 17 and the second wires 18 in the braided body 16 are radially overlapped and joined at the crossing parts 19 such that the one of either the first wires 17 and the second wires 18 are arranged radially inside the other of the wires. In addition, recess parts 19b are provided at least on the tip side of the radially outer surfaces 18a of the crossing parts 19. The tip parts of one of the wires do not protrude from width-directional side surfaces 19a on the tip side of the crossing parts 19 (the width-directional side surfaces of the portions of the other of the wires including the crossing parts 19). As shown in FIG. 16, a maximum thickness of the crossing part 19 between the first wire 17 and the second wire 18 is the sum of a thicknesses $L_{17}$ of the first wire 17 and a thickness $L_{18}$ of the second wire 18 ($L_{17}+L_{18}$). In a portion including the recess parts 19b, the thickness of the crossing part 19 gradually decreases toward the width-directional side surface 19a on the tip side.

In the manufacturing method of a catheter having such recess parts 19b, as in each example described above, the cutting step is performed after the arranging step of arranging the braided body 16 on the cylindrical outer circumferential surface 14a of the inner layer 14, and the coating step of coating the outer circumferential side of the inner layer 14 and the braided body 16 with the coating member 34 (FIG. 5A). In the cutting step, laser irradiation is performed, from the outside of the coating member 34, on an area including: portions of one of either the first wires 17 and the second wires 18 which are on the inner circumferential side at the crossing parts 19 between the first wires 17 and the second wires 18, the portions being located closer to the tip side than the crossing parts 19; and the tip side of the radially outer surfaces of the other of the wires, which are on the outer circumferential side at the crossing parts 19 in the braided body 16. Then, the one of the wires are cut, while the first wires 17 and the second wires 18 are welded. At this time, the irradiation position and the irradiation energy of the laser light are adjusted so that the energy of the laser light melts and cuts the portions of one of the wires, located closer to the tip side than the crossing parts 19, and also melts the tip side of the radially outer surfaces 18a of the crossing parts 19 to form the recess parts 19b. At this time, as shown in FIG. 15, the other of the wires may also be irradiated with the laser light, so that the recess parts 19b are formed not only at the crossing parts 19 but also at a continuous portion from the crossing parts 19 toward an axial center side in the longitudinal direction of the other of the wires. After the cutting step, as in each example described above, the coating removing step of removing the coating member 34 and the wire removing step of removing extra parts of the first wires 17 are performed. FIG. 15 shows the joint part at the crossing part 19 where the first wire 17 is located on the inner circumferential side of the second wire 18, though the joint part at the crossing part where the second wire 18 is arranged on the inner circumferential side of the first wire 17 is also formed in a similar manner.

The catheter in this example can prevent thick tip parts of one of the wires from being formed in the range from the width-directional side surfaces 19a to the tip side of the other of the wires on the outer circumferential side in the crossing parts 19. Therefore, it becomes unnecessary to increase the thickness of the outer layer of the catheter so as to prevent the braided body 16 from protruding from the outer circumferential surface of the outer layer, and it is also possible to suppress the unevenness on the outer circumferential surface of the outer layer 30 in the radial direction. In this example, the other configurational aspects and effects are similar to those in FIGS. 1 to 11. Note that in this example, the recess parts 19b may be formed so as to reach the inner circumferential side surfaces of the crossing parts. Moreover, one part of the braided body of the catheter may have a configuration where the tip parts 22 of one of the wires are formed from the side surfaces of the crossing parts 19 as shown in FIG. 8, and another part of the braided body may have a configuration where the recess parts 19b are formed on the side surfaces of the crossing parts 19 as shown in FIG. 15.

In each of the above examples, configurations other than the shrink tube or a combination of the inner coating part and the outer coating part may be used for the coating member. For example, a transparent or translucent cellophane tape or a translucent low adhesive tape may be wrapped around the outer circumferential side of the intermediate member as the coating member, so as to adhere to the outer circumferential side of the braided body 16. As a coating member, a long member in a cylindrical shape or with a circular arc-shaped cross section may be used.

In each of the above examples, the configuration where the catheter 10 has the inner layer 14 provided on the inner circumferential side of the braided body 16 has been described, though the catheter may be configured without the inner layer. In this case, the braided body, in the state of being wound around a shaft part formed on a jig, is irradiated with laser light where necessary so as to be cut and melted. In this case, the shaft part of the jig corresponds to the inner member. Also, in order to make it easier to pull out the braided body from the jig after cutting and welding, the shaft part of the jig is coated with resin coating as an antifriction material in advance before the braided body is wound. After the braided body is formed, the outer layer is formed on the outer circumferential side of the braided body. According to this configuration, since there is no need to provide an inner layer in the catheter, the cost of the catheter can be reduced by reducing the number of components.

In the configuration of each of the above examples, description has been given of the case where the cutting step in the manufacturing method of a catheter is performed to cut one of the first wires and the second wires by irradiation of laser light while welding the first wires and the second wires. However, the cutting step may be performed to cut one of the first wires and the second wires by irradiation of laser light, and a welding step may be performed to weld the first wires and the second wires separately from the cutting step. In the configuration of each of the above examples, description has been given of the case where the first wires 17 and the second wires 18 are formed by metal wires of the same metallic material, though the first wires 17 and the second wires 18 may be formed by different metallic materials.

In the above description, an extra part at the tip part of the braided body 16, located at the distal end side of the distal shaft 12, is cut and removed by laser irradiation, and the tips parts of the first wires 17 and the second wires 18 in the cut part are further welded to each other so as to prevent the braided body 16 from being unbraided at the cut portions. On the other hand, in the configuration of the present invention, the extra part may be removed at the tip part of the braided body 16, located at the distal end side of the distal shaft 12, and the tip parts of the first wires 17 and the second wires 18 in the cut part may be welded to each other so as to prevent the braided body 16 from being unbraided at the cut portions. In addition, in each of the above examples, description has been given of the case where the catheter manufactured by the manufacturing method of the present invention is a guide extension catheter, though the catheters manufactured by the manufacturing method of the present invention are not limited to the guide extension catheter, and may be a variety of catheters with the braided body provided inside the outer layer.

REFERENCE SIGNS LIST

10 Guide extension catheter (catheter), 12 Distal shaft, 14 Inner Layer, 14a Cylindrical outer circumferential surface, 15 Lumen, 16, 16a Braided body, 17 First wire, 18 Second wire, 18a Radially outer surface, 19 Crossing part, 19a width-directional side surface, 19b recess part, 20 Intermediate part, 21 Extra portion, 22 Tip part of one of the wires, 22a Radially outer surface, 23 One-side run-over part, 24 Other-side run-over part, 30 Outer layer, 31 Tip chip, 34 Coating member, 35 Sheet, 36 Magnet, 37 Plate, 40a, 40b Joint part, 41 Coating member, 42 Inner coating part, 43 Outer coating part, 50 Proximal shaft, 60 Laser light, 100 Guiding catheter, 102 Coronary artery, 106 Stent delivery catheter.

The invention claimed is:

1. A catheter, comprising:
a braided body having first wires, and second wires crossing the first wires; and
an outer layer provided on an outer circumference of the braided body, wherein
in the braided body, the first wires and the second wires are radially overlapped and joined at crossing parts such that one of the first wires and the second wires are arranged radially inside the other of the first wires and the second wires, and
the crossing parts have recess parts on a tip side of at least radially outer surfaces of the crossing parts, and tip parts of the one of the first wires and the second wires do not protrude from at least a part of tip-side lateral surfaces of the crossing parts.

2. The catheter according to claim 1, wherein radially outer surfaces of the tip parts of the one of the first wires and the second wires, protruding to a tip side from width-directional side surfaces of portions of the other of the first wires and the second wires including the crossing parts, are arranged at identical radial direction positions on radially outer surfaces of the other of the first wires and the second wires, or arranged radially inside at the crossing parts.

3. The catheter according to claim 2, wherein the first wires and the second wires are formed by metal wires made of the same metallic material.

4. The catheter according to claim 2, wherein the tip parts of the one of the first wires and the second wires have one-side run-over parts extending so as to be away from the crossing parts along a longitudinal direction of the other of the first wires and the second wires.

5. The catheter according to claim 2, wherein the tip parts of the other of the first wires and the second wires have other-side run-over parts running out so as to protrude from the crossing parts in a longitudinal direction of the other of the first wires and the second wires.

* * * * *